United States Patent [19]

Tobler

[11] Patent Number: 5,026,899
[45] Date of Patent: Jun. 25, 1991

[54] ACYLCYLOHEXANEDIONES AND THE OXIME ETHERS THEREOF WITH HERBICIDAL AND PLANT GROWTH REGULATING PROPERTIES

[75] Inventor: Hans Tobler, Allschwil, Switzerland

[73] Assignee: Ciba-Geigy Corporation, Ardsley, N.Y.

[21] Appl. No.: 450,128

[22] Filed: Dec. 13, 1989

Related U.S. Application Data

[60] Division of Ser. No. 159,803, Feb. 24, 1988, Pat. No. 4,909,835, which is a continuation-in-part of Ser. No. 39,039, Apr. 16, 1987, abandoned.

[30] Foreign Application Priority Data

Apr. 24, 1986 [CH] Switzerland ................ 1664/86

[51] Int. Cl.$^5$ ............................. C07C 69/74
[52] U.S. Cl. ................. 560/122; 558/412; 560/1; 560/9; 560/18; 560/20; 560/55; 560/65; 560/73; 560/105; 560/107; 560/123; 560/124; 560/152; 560/187; 560/228; 560/231
[58] Field of Search ............... 560/122, 231, 1, 9, 560/18, 20, 55, 65, 73, 105, 107, 123, 124, 152, 187, 228; 558/412

[56] References Cited

U.S. PATENT DOCUMENTS

| | | | |
|---|---|---|---|
| 4,249,937 | 2/1981 | Iwataki | 71/97 |
| 4,440,566 | 4/1984 | Luo | 71/98 |
| 4,517,013 | 5/1985 | Becker | 71/98 |
| 4,617,050 | 10/1986 | Jahn | 71/98 |
| 4,626,276 | 12/1986 | Luo | 71/103 |

FOREIGN PATENT DOCUMENTS 90262 10/1983 European Pat. Off.
99534 2/1984 European Pat. Off.

OTHER PUBLICATIONS

Roberts, "Basic Principles of Organic Chemistry", pp. 113–114, (1965).
Fieser, "Organic Chemistry", pp. 49–50, (1944).
Takyuki, Agr. Biol. Chem., 37, pp. 262–368, (1973).

Primary Examiner—Michael L. Shippen
Attorney, Agent, or Firm—Kevin T. Mansfield; Edward McC. Roberts

[57] ABSTRACT

The invention relates to novel 2-acyl-1,3-cyclohexanediones and the oxime ethers thereof with herbicidal and plant growth regulating properties.

The novel 2-acyl-1,3-cyclohexanediones and the oxime ethers thereof are of the formula I

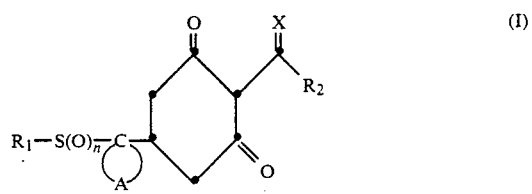

wherein
A is a 2- or 7-membered alkylene bridge, or a 3- to 7-membered alkenylene bridge which may be mono- or polyunsaturated,
n is 0, 1 or 2,
$R_1$ is $C_1$–$C_4$alkyl or benzyl,
$R_2$ is $C_1$–$C_6$alkyl which is unsubstituted or substituted by halogen, $C_1$–$C_4$alkoxy or $C_1$–$C_4$alkylthio; or is $C_3$–$C_6$cycloalkyl; or phenyl, benzyl or phenylethyl, the phenyl ring of each of which may be substituted by halogen, $C_1$–$C_4$alkyl, $C_1$–$C_4$alkoxy, $C_1$–$C_4$alkylthio, $C_1$–$C_4$haloalkyl, $C_1$–$C_4$haloalkoxy, cyano or nitro,
X is oxygen or a radical —$NOR_3$, and
$R_3$ is $C_1$–$C_6$alkyl, $C_1$–$C_6$haloalkyl, $C_3$–$C_6$alkenyl, $C_3$–$C_6$haloalkenyl or $C_3$–$C_6$alkynyl and to the metal and quaternary ammonium salts of these compounds.

The invention also relates to processes for the preparation of these acylcyclohexanediones and of the oxime ethers thereof, as well as to novel intermediates.

4 Claims, No Drawings

ACYLCYLOHEXANEDIONES AND THE OXIME ETHERS THEREOF WITH HERBICIDAL AND PLANT GROWTH REGULATING PROPERTIES

This is a division of application Ser. No. 159,803 filed on Feb. 24, 1988, now U.S. Pat. No. 4,909,835 which is a continuation-in-part of application Ser. No. 039,039 filed Apr. 16, 1987, now abandoned.

The present invention relates to novel 2-acyl-1,3-cyclohexanediones and the oxime ethers thereof with herbicidal and plant growth regulating properties, to the preparation of said 2-acyl-1,3-cyclohexanediones and of the oxime ethers thereof, to compositions containing these novel substances and also to the use of said substances or of compositions containing them for controlling weeds and for regulating plant growth.

The novel 2-acyl-1,3-cyclohexanediones and the oxime ethers thereof are of the formula I

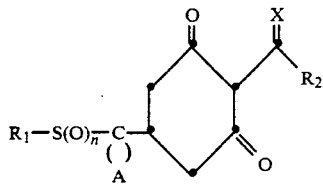

wherein

A is a 2- to 7-membered alkylene bridge, or a 3- to 7-membered alkenylene bridge which may be mono- or polyunsaturated, n is 0, 1 or 2, $R_1$ is $C_1$–$C_4$alkyl or benzyl, $R_2$ is $C_1$–$C_6$alkyl which is unsubstituted or substituted by halogen, $C_1$–$C_4$alkoxy or $C_1$–$C_4$alkylthio; or is $C_3$–$C_6$cycloalkyl; or phenyl, benzyl or phenylethyl, the phenyl ring of each of which may be substituted by halogen, $C_1$–$C_4$alkyl, $C_1$–$C_4$alkoxy, $C_1$–$C_4$alkylthio, $C_1$–$C_4$haloalkyl, $C_1$–$C_4$haloalkoxy, cyano or nitro, X is oxygen or a radical —$NOR_3$, and $R_3$ is $C_1$–$C_6$alkyl, $C_1$–$C_6$haloalkyl, $C_3$–$C_6$alkenyl, $C_3$–$C_6$haloalkenyl or $C_3$–$C_6$alkynyl.

The invention also relates to the isomers, enantiomers and diastereoisomers of the compounds of formula I, as well as to the salts of said compounds with metals and quaternary ammonium bases.

In the above definitions alkyl by itself or as moiety of another substituent such as alkoxy, alkylthio, haloalkyl or haloalkylthio shall be understood as comprising straight chain and branched radicals, e.g. methyl, ethyl, propyl, isopropyl, butyl, isobutyl, sec-butyl, tert-butyl, as well as all stereosiomers of the higher homologues. Alkenyl and alkynyl also comprise straight chain and branched radicals, as well as the cis- and trans-forms thereof, e.g. allyl, methallyl, butenyl, methylbutenyl, dimethylbutenyl, ethynyl, propynyl, butynyl, methylbutynyl, dimethylbutynyl.

Cycloalkyl radicals $R_2$ or cycloalkyl radicals which are formed by the carbon atom and the alkylene bridge A comprise cyclopropyl, cyclobutyl, cyclopentyl, cyclohexyl, cycloheptyl and cyclooctyl. Cycloalkenylene radicals formed by the carbon atom and the alkenylene bridge A may be mono- or polyunsaturated, e.g. cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl and cyclooctatrienyl. These radicals may be substituted by up to 5 methyl groups.

Halogen shall be understood as meaning fluorine, chlorine, bromine or iodine atoms.

The 2-acyl-1,3-cyclohexanediones, and the oxime ethers thereof, of formula I are distinguished by good herbicidal and plant growth regulating properties. Among those compounds which are to be singled out for particular mention on account of their activity are the following groups:

Acylcyclohexanediones of formula I
wherein

A is a 2- to 7-membered alkylene bridge, n is 0, 1 or 2, $R_1$ is $C_1$–$C_4$alkyl or benzyl, $R_2$ is $C_1$–$C_6$alkyl which is unsubstituted or substituted by halogen, $C_1$–$C_4$alkoxy or $C_1$–$C_4$alkylthio; or is $C_3$–$C_6$cycloalkyl; or phenyl, benzyl or phenylethyl, the phenyl ring of each of which may be substituted by halogen, $C_1$–$C_4$alkyl, $C_1$–$C_4$alkoxy, $C_1$–$C_4$alkylthio, $C_1$–$C_4$haloalkyl, $C_1$–$C_4$haloalkoxy, cyano or nitro, and X is oxygen, preferably the compounds 5-(1-methylthiocyclobutan-1-yl)-2-(2,4-dichlorobenzoyl)cyclohexane-1,3-dione, 5-(1-methylthiocyclobutan-1-yl)-2-n-butyrylcyclohexane-1,3-dione, 5-(1-methylthiocyclobutan-1-yl)-2-cyclopropylcarbonylcyclohexane-1,3-dione, 5-(1-methylthiocyclobutan-1-yl)-2-(2,3-dichlorobenzoyl)cyclohexane-1,3-dione, 5-(1-methylsulfonylcyclobutan-1-yl)-2-n-butyrylcyclohexane-1,3-dione, 5-(1-methylthiocyclopropan-1-yl)-2-propionylcyclohexane-1,3-dione, 5-(1-ethylthiocyclopropan-1-yl)-2-propionylcyclohexane-1,3-dione and 5-(1-methylthiocyclopropan-1-yl)-2-n-butyrylcyclohexane-1,3-dione.

Oxime ethers of acylcyclohexanediones of formula I also to be singled out for particular mention are those wherein A is a 2- to 7-membered alkylene bridge, n is 0, 1 or 2, $R_1$ is $C_1$–$C_4$alkyl or benzyl, $R_2$ is $C_1$–$C_6$alkyl which is unsubstituted or substituted by halogen, $C_1$–$C_4$alkoxy or $C_1$–$C_4$alkylthio, X is the radical —$NOR_3$, and $R_3$ is $C_1$–$C_6$alkyl, $C_3$–$C_6$haloalkyl, $C_3$–$C_6$alkenyl, $C_3$–$C_6$haloalkenyl or $C_3$–$C_6$alkynyl, preferably the compounds 5-(1-methylthiocyclobutan-1-yl)-2-(1'-ethoximinobutyryl)cyclohexane-1,3-dione, 5-(1-methylthiocyclopropan-1-yl)-2-(1-ethoximinobutyryl)cyclohexane-1,3-dione, 5-(1-methylthiocyclohexan-1-yl)-2-(1-ethoximinobutyryl)cyclohexane-1,3-dione, 5-(1-methylthiocyclobutan-1-yl)-2-(1'-allyloxyiminobutyryl)cyclohexane-1,3-dione, 5-(1-methylthiocyclopentan-1-yl)-2-(1-ethoximinobutyryl)cyclohexane-1,3-dione, 5-(1-methylthiocyclopropan-1-yl)-2-[1-(trans-3-chloroallyloximino)-n-butyryl]cyclohexane-1,3-dione, 5-(1-methylthiocyclopropan-1-yl)-2-[1-(trans-3-chloroallyloximino)propionyl]cyclohexane-1,3-dione, 5-(1-methylthiocyclopropan-1-yl)-2-[1-(cis-3-chloroallyloximino)propionyl]cyclohexane-1,3-dione, 5-(1-ethylthiocyclopropan-1-yl)-2-[1-(trans-3-chloroallyloximino)propionyl]cyclohexane-1,3-dione and 5-(1-ethylthiocyclopropan-1-yl)-2-[1-(trans-3-chloroallyloximino)-n-butyryl]cyclohexane-1,3-dione.

These compounds may also be obtained in their tautomeric forms or as salts, in particular alkali metal and alkaline earth metal salts and also manganese, copper, zinc and iron salts.

The salts correspond to the formula Ic

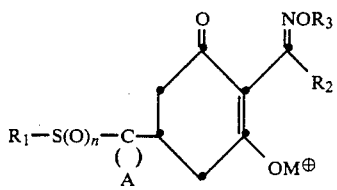

wherein A, n, $R_1$, $R_2$ and $R_3$ have the meaning given under formula I and $M^\oplus$ is the ion-equivalent of a metal or a quaternary ammonium ion. Good activity showed sodium-2-[1-(3-trans-chlorallyloxyamino)-propylidene]-3-oxo-5-(1-methylthio-1-cyclopropyl)-cyclohex-1-en-1-olate.

The acylcyclohexanediones and the oxime ethers thereof of the present invention are prepared in a manner known per se by reacting a 1,3-cyclohexanedione which is suitably substituted in the 5-position by the radical with an acid chloride or acid cyanide, and, if desired, further reacting the resultant 2-acyl-1,3-cyclohexanedione with a hydroxylamine.

A first process for the preparation of the acylcyclohexanediones, and of the oxime ethers thereof, of formula I comprises reacting a 1,3-cyclohexanedione derivative of formula II

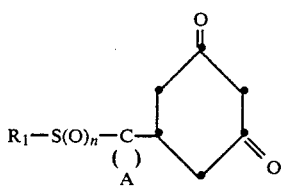

wherein A, n and $R_1$ are as defined for formula I, with an acid halide or acid anhydride of formula III

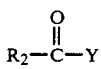

wherein Y is a halogen atom or a radical

and $R_2$ is as defined for formula I, in an inert organic solvent and in the presence of the equimolar amount of a base, and rearranging the resultant cyclohexanone ester of formula IV

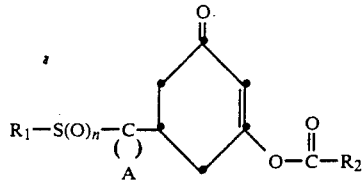

wherein A, n, $R_1$ and $R_2$ are as defined for formula I, in an inert organic solvent and in the presence of a catalyst, to give the 2-acyl-1,3-cyclohexanedione derivative of formula (Ia)

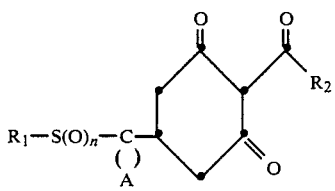

wherein A, n, $R_1$ and $R_2$ are as defined for formula I, and, if desired, reacting said derivative of formula Ia with a hydroxylamine. hydrochloride of formula V

$H_2NOR_3 \cdot HCl$     (V)

wherein $R_3$ is as defined for formula I, in an inert organic solvent and in the presence of the equimolar amount of a base, to give the oxime ether of formula Ib

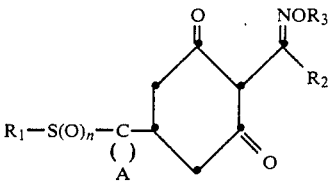

wherein A, n, $R_1$, $R_2$ and $R_3$ are as defined for formula I.

The rearrangement of the cyclohexanone ester of formula IV to give the 2-acylcyclohexanedione derivative of formula Ia is effected e.g. by treatment in an inert organic solvent and in the presence of a catalyst or in an organic base as solvent. Examples of suitable catalysts are pyridine, 4-aminopyridine, 4-(dimethylamino)pyridine, aluminium(III) chloride in methylene chloride, collidine or lutidine, and also cyanohydrines in the presence of a nitrogen base, such as e.g. triethylamine.

The cyclohexanone esters of formula IV are novel compounds. They and the preparation thereof also constitute an object of the present invention.

A second more direct process for the preparation of acylcyclohexanediones, and of the oxime ethers thereof, of formula I comprises reacting a 1,3-cyclohexanedione derivative of formula II

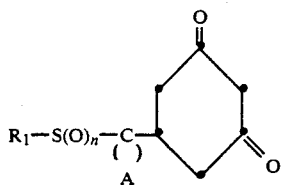

wherein A, n and $R_1$ are as defined for formula I, with an acid cyanide of formula VI

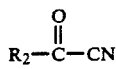

wherein $R_2$ is as defined for formula I, in an inert organic solvent or diluent and in the presence of zinc chloride and a nitrogen base, and, if desired, reacting the resultant 2-acyl-1,3-cyclohexanedione derivative of formula Ia

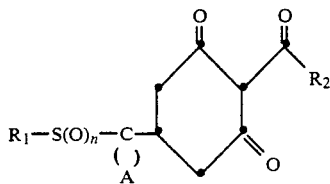

wherein A, n, $R_1$ and $R_2$ are as defined for formula I, with a hydroxylamine. hydrochloride of formula V $H_2NOR_3 \cdot HCl$ (V)

wherein $R_3$ is as defined for formula I, in an inert organic solvent and in the presence of the equimolar amount of a base, to give the oxime ether of formula Ib

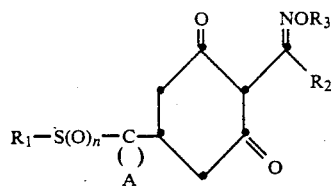

wherein A, n, $R_1$, $R_2$ and $R_3$ are as defined for formula I.

The salts of the acylhexanedione oxime ether of the formula Ic

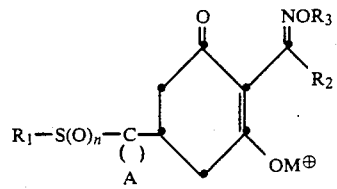

wherein A, n, $R_1$, $R_2$ and $R_3$ have the meaning given under formula I and $M^\oplus$ is the ion equivalent of a metal or a quaternary ammonium ion, by reacting a 2-acyl-1,3-cyclohexanedione oxime ether of the formula Ib

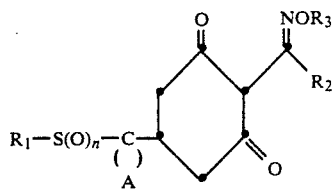

wherein A, n, $R_1$, $R_2$ and $R_3$ have the above given meaning, in an inert solvent, with at least the equimolar amount of a hydroxide of the formula XVII $M^\oplus$—OH (XVII)

wherein $M^\oplus$ is the ion-equivalent of a metal or a quaternary ammonium ion and eliminating the water formed during the condensation, e.g. by destillation.

Suitable organic solvents for these reactions are, in particular, aromatic compounds such as benzene or toluene, hydrohalogen compounds such as chloroform, dichloroethane or carbon tetrachloride, or esters such as ethyl acetate.

The reaction temperatures are in the range from room temperature to the boiling point of the reaction mixture. During the addition of acid chloride it may prove advisable to cool the reaction vessel.

Both inorganic and organic bases are suitable, e.g. pyridine, 4-aminopyridine, 4-dimethylaminopyridine, collidine, triethylamine, ammonium carbonate, sodium carbonate, potassium carbonate or calcium carbonate or the corresponding bicarbonates.

Such reactions are known. For the reaction with the acid halide or acid anhydride of formula III see Tetrahedron Letters 29 (1973) 249 or Synthesis 1978, 925; and for the reaction with the acid cyanide of formula V see published European patent application No. 90 262.

The starting cyclohexanediones of formula II are prepared in a multistage process.

An unsaturated methyl ketone of formula VII

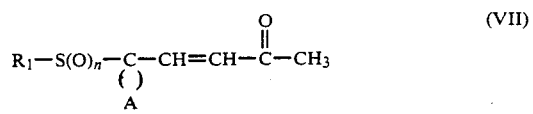

wherein A, n and $R_1$ are as defined for formula I, is reacted with a malonic acid diester of formula VIII

wherein R is a $C_1$-$C_6$alkyl radical or benzyl, in an absolute, inert organic solvent, in the presence of alkali metal methylate and at the reflux temperature of the solvent, to give the cyclohex-1-en-2-ol-4-one ester of formula IX

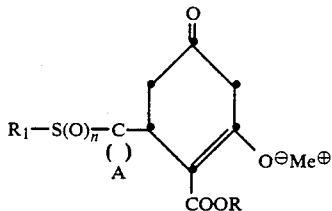

(IX)

wherein A, n and R₁ are as defined for formula I, R is a C₁-C₆alkyl radical or benzyl and Me⊕ is an alkali metal ion, saponifying said ester in the presence of sodium hydroxide solution or potassium hydroxide solution, washing the saponified ester with acid, then decarboxylating the resultant 2,4-cyclohexanedione acid derivative of formula X

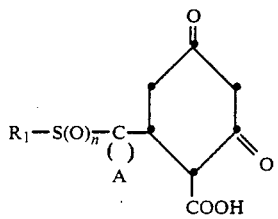

(X)

wherein A, n and R₁ are as defined for formula I, in an inert solvent, and isolating from the reaction mixture the cyclohexanedione of formula II required as starting material

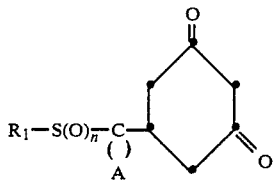

(II)

wherein A, n and R₁ are as defined for formula I.

The reaction of the unsaturated methyl ketone of formula VII with the malonic acid diester of formula VIII is carried out in an absolute solvent and in the presence of, preferably, sodium methylate or potassium methylate. Preferred malonic acid esters are the ethyl and methyl esters. The saponification and subsequent precipitation of the acid are effected in aqueous medium. The 2,4-cyclohexanedione-1-carboxylic acid derivative of formula X is then boiled in a solvent, e.g. water, toluene or xylene, or in a chlorine-containing solvent, e.g. methylene chloride or chloroform, until the formation of carbonic acid ceases.

Another method of preparing the 1,3-cyclohexanedione derivatives of formula II comprises condensing an aldehyde of formula XI

wherein A, n and R₁ are as defined for formula I, with malonic acid, in a basic solvent, to give the unsaturated acid of formula XII

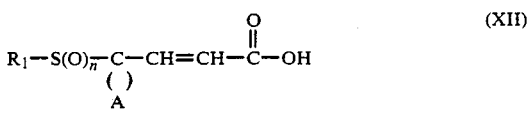

wherein A, n and R₁ are as defined for formula I. This acid is then esterified in known manner with an alkanol R—OH, wherein R is C₁-C₆alkyl or benzyl, and the resultant ester of formula XIV is then ring-closed with an acetoacetic acid alkyl ester of formula XV, in an absolute solvent and in the presence of sodium methylate or potassium methylate, in accordance with the following reaction scheme:

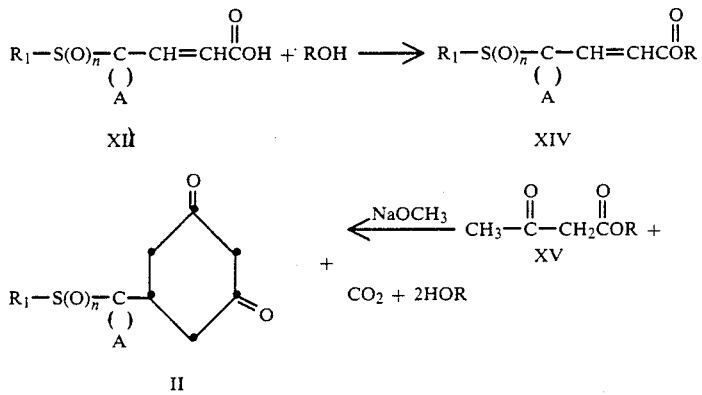

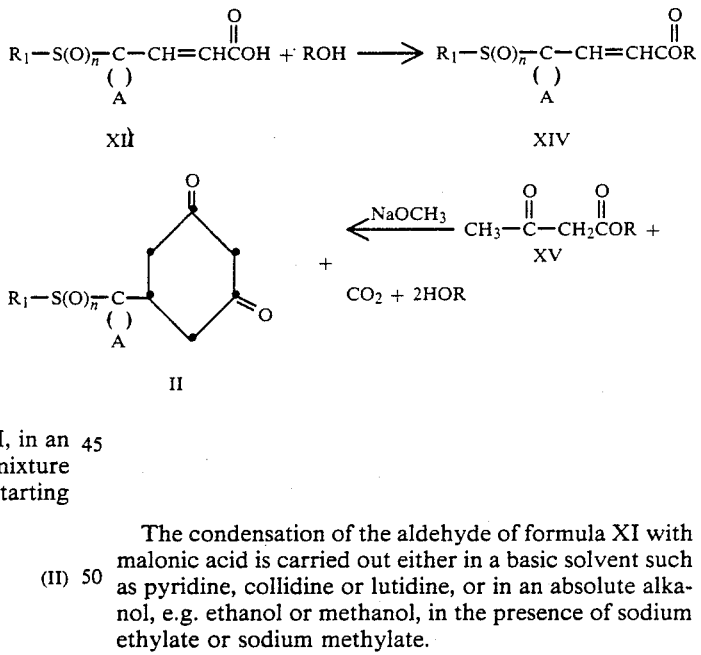

The condensation of the aldehyde of formula XI with malonic acid is carried out either in a basic solvent such as pyridine, collidine or lutidine, or in an absolute alkanol, e.g. ethanol or methanol, in the presence of sodium ethylate or sodium methylate.

The 1,3-cyclohexanedione derivatives of formula II are novel products. They and the preparation thereof constitute an object of the present invention.

The starting methyl ketones of formula VII are prepared by condensing aldehydes of formula XI with acetone and subsequently dehydrating the β-hydroxyketone obtained as condensation product.

The reaction can be illustrated by the following scheme:

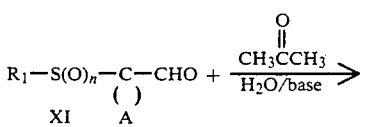

-continued

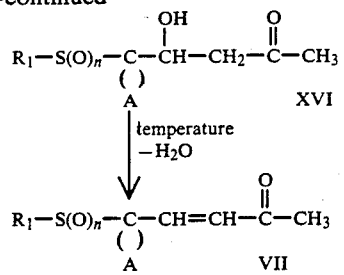

The condensation is effected in aqueous medium and in the presence of a base, e.g. sodium hydroxide solution or potassium hydroxide solution, advantageously at elevated temperature, e.g. at the boiling point of the reaction mixture.

The 1-alkylthiocycloalkylcarbaldehydes, 1-alkylsulfinylcycloalkylcarbaldehydes and 1-alkylsulfonylcycloalkylcarbaldehydes of formula IX are known; the preparation thereof is described for example in German Offenlegungsschrift No. 2,120,908, or they can be prepared by a procedure analogous to that disclosed in German Offenlegungsschrift No. 2,403,236.

The unsaturated methyl ketones of formula VII are novel products. They and the preparation thereof constitute an object of the present invention.

The process for the preparation of the unsaturated methyl ketones of formula VII

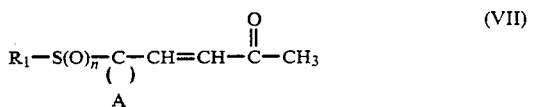

wherein A, n and $R_1$ are as described for formula I, comprises condensing an aldehyde of formula XI

wherein A, n and $R_1$ are as defined for formula I, with acetone, in basic aqueous medium, then boiling the condensation product for several hours at reflux and subsequently isolating the resultant unsaturated methyl ketone from the reaction mixture.

A similar process for the preparation of unsaturated ketones is described for example in Agr. Biol. Chem. 37 (1973), 261.

The described preparatory processes, including all partial steps, constitute an important object of the present invention. The novel compounds are solids or oils whose use poses no problems.

The compounds of formula I have herbicidal and plant growth regulating properties and are suitable e.g. for selectively controlling grasses in crops of useful plants. The trans- and cis-3-chloroallyl oxime ethers are particularly active, especially the trans-isomers.

When used at low rates of application, the compounds of formula I have good growth inhibiting and selective herbicidal properties which make them preeminently suitable for use in crops of useful plants, in particular in sugar beet, cereals, cotton, soybeans, maize and rice. In some cases damage is also caused to weeds which have only been controlled up to now with total herbicides.

The compounds of formula I also have good plant growth regulating properties.

Surprisingly, it has now been found that the novel compounds of formula I and compositions containing these compounds are characterised in particular by their selective influence on plant metabolism. This selective influence on the physiological processes of plant development makes it possible to use the compounds of formula I for different purposes, especially for those in connection with increasing the yield of useful plants, with facilitating harvesting, and with labour-saving in measures taken in crops of cultivated plants.

Previous experience with plant growth regulators has shown that they are able to induce one or more different responses in the plants. These different responses depend substantially on the time of application, based on the state of development of the seed or plant, as well as on the concentrations of active substance applied to the plants or to the locus thereof and on the nature of application. Growth regulators should at all events induce positive responses in the cultivated plants in the desired manner.

Plant growth regulators may be used e.g. for inhibiting vegetative plant growth. Such a growth inhibition is of economic interest, inter alia, in respect of grasses, as the frequency of cutting in flower gardens, parks, sports fields or road shoulders can thereby be reduced. Of importance too is the inhibition of growth of herbaceous and ligneous plants on road shoulders and near transmission lines, or generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals, thereby also counteracting lodging.

Inhibition of the vegetative growth of many cultivated plants permits more plants to be sown in a crop area, so that a higher yield may be obtained per unit of area.

A further mechanism of yield increase using growth regulators resides in the fact that nutrients are able increasingly to promote flower formation and fruiting, whereas vegetative growth is inhibited.

Growth regulators are also frequently able to promote vegetative growth. This is very beneficial when the vegetative parts of plants are to be harvested. However, promotion of vegetative growth can also result simultaneously in promotion of generative growth, so that e.g. more or larger fruit is formed.

Yield increases may also often be obtained by influencing the plant metabolism without any visible changes in vegetative growth. Growth regulators can also induce a change in the composition of plants, so that the quality of the harvest produce is improved. For example, it is possible to increase the sugar content of sugar beet, sugar cane, pineapples and citrus fruit, or to increase the protein content of soybeans or cereals.

The use of growth regulators can lead to the formation of parthenocarpic fruit. The sex of blossoms can also be influenced.

The production or flow of secondary plant substances can also be positively influenced by growth regulators, for example the stimulation of the flow of latex in rubber trees.

During plant growth, the development of side-shoots can also be promoted by the chemical interruption of apical dominance using growth regulators. This is of interest e.g. in the propagation of plant cuttings. However, it is also possible to inhibit the growth of side-shoots, e.g. in tobacco plants after decapitation in order to prevent the formation of side-shoots, and thus to promote leaf growth.

With growth regulators it is also possible to speed up or delay the ripening of harvest products before or after harvesting. This is particularly advantageous, because a best possible accommodation to market requirements can thereby be achieved. In addition, growth regulators can often improve the colour of fruit. With the aid of growth regulators it is also possible to concentrate ripening at a particular time. The conditions are thus created for a complete mechanical harvesting of e.g. tobacco, tomatoes or coffee, or for manual harvesting, in only one single operation.

The application of growth regulators can also make it possible to influence the dormancy of seeds and buds of plants, i.e. the endogenic annual rhythm, so that plants, e.g. pineapples, or ornamentals in nurseries, germinate, sprout or blossom at a time when they would normally not tend to do so.

With growth regulators it is also possible to delay budding or the germination of seeds, e.g. in order to avoid damage by late frosts in areas endangered thereby. Conversely, root growth and/or the formation of shoots can be stimulated, so that growth may be restricted to a shorter period.

Growth regulators can also impart halophilic properties to cultivated plants. The conditions are thus created for cultivating plants in salty soil.

Growth regulators can also induce resistance to frost and drought in plants.

Under the influence of growth regulators, the ageing (senescence) of plants or parts of plants can be inhibited or delayed. Such an action can be of great economic importance, as the storability of treated parts of plants or whole plants such as fruit, berries, vegetables, salads or ornamentals can be improved or prolonged after harvesting. Likewise, a substantial yield increase can be obtained by treating cultivated plants by prolonging the phase of photosynthetic activity.

A further important field of use for growth regulators is the inhibition of excessive growth of tropical cover crops. In tropical and subtropical monocultures, e.g. in palm tree plantations, cotton and maize fields etc., cover crops, especially species of leguminosae, are often planted together with the actual cultivated plants with the object of maintaining or improving the quality of the soil (prevention of desiccation, supplying nitrogen) and for preventing erosion. By applying the compounds of this invention it is possible to control the growth of these cover crops and so to keep the growth in height of these plants at a low level, thus ensuring healthy growth of the cultivated plants and the maintenance of favourable soil conditions.

The compounds of formula I are normally applied in the form of compositions and can be applied to the crop area or plant to be treated, simultaneously or in succession, with further compounds. These further compounds can be both fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I or an agrochemical composition containing at least one of said compounds, is foliar application. The number of applications and the rate of application depend on the manner in which growth is to be influenced. However, the compounds of formula I can also penetrate the plant through the roots via the soil (systemic action) by drenching the locus of the plant with a liquid composition, or by applying the compounds in solid form to the soil, e.g. in granular form (soil application). The compounds of formula I may also be applied to seeds (coating) by either impregnating the seeds with a liquid formulation of the compound, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are in general from 10 g to 5 kg of active ingredient (a.i.) per hectare, preferably from 100 g to 3 kg a.i./ha, most preferably from 200 g to 1000 g a.i./ha.

The formulations, i.e. the compositions, preparations or mixtures containing the compound (active ingredient) of formula I and, where appropriate, a solid or liquid adjuvant, are prepared in known manner, e.g. by intimately mixing and/or grinding the active components with extenders, e.g. with solvents, solid carriers, and optionally surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are e.g. the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty solfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamino-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp. Ridgewood, N.J., 1979;

M. and J. Ash, "Encyclopedia of Surfactants", Vol. I-III, Chemical Publishing Co. Inc., New York, 1980-81;

H Stache, "Tensid Taschenbuch" (Handbook of Surfactants), 2nd edition, Carl Hanser Verlag, Munich/Vienna 1981.

The formulations of this invention usually contain 0.1 to 99%, preferably 0.1 to 95%, of a compound of formula I, 1 to 99% of a solid or liquid adjuvant, and 0 to 25%, preferably 0.1 to 25%, of a surfactant.

Preferred formulations are composed in particular of the following constituents (%=percentage by weight):

SOLUTIONS compound of formula I: 5 to 95%, preferably 10 to 80%
solvent: 95 to 5%, preferably 90 to 0%
surfactant: 1 to 30%, preferably 2 to 20%

EMULSIFIABLE CONCENTRATES compound of formula I: 10 to 50%, preferably 10 to 40%
surfactant: 5 to 30%, preferably 10 to 20%
liquid carrier: 20 to 95%, preferably 40 to 80%

DUSTS compound of formula I: 0.5 to 10%, preferably 2 to 8%
solid carrier: 99.5 to 90%, preferably 98 to 92%

SUSPENSION CONCENTRATES compound of formula I: 5 to 75%, preferably 10 to 50%
water: 94 to 25%, preferably 90 to 30%
surfactant: 1 to 40%, preferably 2 to 30%

WETTABLE POWDERS compound of formula I: 5 to 90%, preferably 10 to 80% and most preferably 20 to 60%
surfactant: 0.5 to 20%, preferably 1 to 15%
solid carrier: 5 to 90%, preferably 30 to 70%

GRANULATES compound of formula I: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001% of active ingredient.

The compositions may also contain further ingredients such as stabilisers, antifoams, viscosity regulators, binders, tackifiers, as well as fertilisers and other compounds for obtaining special effects.

Such agrochemical compositions constitute an object of the present invention.

The invention is illustrated by the following non-limitative Examples.

EXAMPLE 1

Preparation of
1-(trans-but-3-en-2-on-4-yl)-1-methylthiocyclobutane
(intermediate)

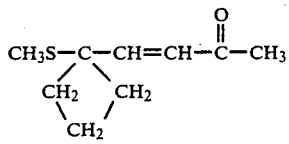

With stirring, 140 ml of aqueous 2N sodium hydroxide solution are added dropwise at 50° C. to a solution of 39 g of cyclobutane-1-methylthio-1-carbaldehyde in 400 ml of acetone over 5 minutes. The mixture is then stirred further for 15 minutes at room temperature and for 8 hours under reflux. Subsequently, the reaction mixture is concentrated, the residue is taken up in ether, the resultant ethereal solution is washed with water and brine and dried, and the ether is evaporated off. The residual oil is distilled at 0.013 mbar, affording 41.5 g of a clear oil with a boiling point of 58° C./0.013 mbar and a content of title product of 96.5% (gas chromatography).

The intermediate methyl ketones of formula VII listed in Table 1 are prepared by procedures analogous to that of this Example.

TABLE 1

$$R_1-S(O)_n-\underset{\underset{A}{(\ )}}{C}-CH=CH-\overset{O}{\overset{\|}{C}}-CH_3 \quad (VII)$$

| Comp. | $R_1$ | n | A | Physical data |
|---|---|---|---|---|
| 1.01 | $CH_3$ | 0 | $(CH_2)_2$ | b.p. 54–55° C./0.013 mbar |
| 1.02 | $C_2H_5$ | 0 | $(CH_2)_2$ | b.p. 66–69° C./0.013 mbar |
| 1.03 | $CH_3$ | 0 | $(CH_2)_3$ | b.p. 58° C./0.013 mbar |
| 1.04 | $C_2H_5$ | 0 | $(CH_2)_3$ | b.p. 70–72° C./0.05 mbar |
| 1.05 | $C_3H_7$-n | 0 | $(CH_2)_3$ | |
| 1.06 | $CH_3$ | 0 | $(CH_2)_4$ | b.p. 74° C./0.013 mbar |
| 1.07 | $C_2H_5$ | 0 | $(CH_2)_4$ | |
| 1.08 | benzyl | 0 | $(CH_3)_4$ | |
| 1.09 | $CH_3$ | 0 | $(CH_2)_5$ | b.p. 85–88° C./0.013 mbar |
| 1.10 | $C_2H_5$ | 0 | $(CH_2)_5$ | b.p. 90–92° C./0.013 mbar |
| 1.11 | $C_3H_7$-n | 0 | $(CH_2)_5$ | |
| 1.12 | $CH_3$ | 0 | $(CH_2)_6$ | |
| 1.13 | $C_2H_5$ | 0 | $(CH_2)_6$ | |
| 1.14 | $C_3H_7$-n | 0 | $(CH_2)_2$ | b.p. 74–79° C./0.013 mbar |
| 1.15 | $CH(CH_3)_2$ | 0 | $(CH_2)_2$ | b.p. 69–72° C./0.013 mbar |
| 1.16 | benzyl | 0 | $(CH_2)_2$ | b.p. 138–141° C./0.013 mbar |
| 1.17 | $CH_3$ | 1 | $(CH_2)_2$ | |
| 1.18 | $CH_3$ | 2 | $(CH_2)_2$ | |
| 1.19 | $CH_3$ | 1 | $(CH_2)_3$ | |
| 1.20 | $CH_3$ | 2 | $(CH_2)_3$ | |

EXAMPLE 2

Preparation of
5-(1-methylthiocyclobutan-1-yl)cyclohexane-1,3-dione
(intermediate)

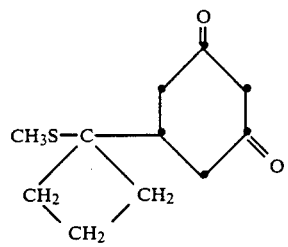

Over 15 minutes, 41 g of 1-(trans-but-3-en-2-on-1-yl)-1-methylthiocyclobutane are added dropwise to a stirred suspension of 33.5 g of dimethyl malonate and 47 g of sodium methylate (30.8% in methanol) in 900 ml of absolute toluene. The pasty reaction mixture is then heated over 5 hours to reflux, with methanol being distilled off until a distillation temperature of 110° C. has been reached. The initially sparingly stirrable reaction mixture thereby turns to a fine suspension. After cooling, this suspension is evaporated to dryness, and the residue is washed with hexane, thus affording 70 g of the sodium salt of 5-(1-methylthiocyclobutan-1-yl)-6-methoxycarbonylcyclohex-1-en-3-on-1-ol of the formula

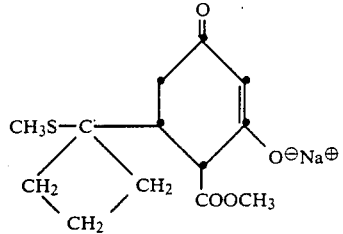

as intermediate.

This intermediate is dissolved in 250 ml of aqueous 2N potassium hydroxide solution, and the resultant solution is stirred for 1½ hours at 80° C. The solution is then allowed to cool. When it reaches 70° C., the slow dropwise addition of 80 ml of concentrated hydrochloric acid is commenced. After cooling, the product precipitates in crystalline form. The product is isolated by filtration and washed with water until the washings are neutral. The product is then dried at 40°–50° C. in a desiccator. Yield: 48 g. Melting point after recrystallisation from ethanol/water: 141°–143° C.

The intermediate 1,3-cyclohexanedione derivatives listed in Table 2 are prepared by procedures analogous to that of this Example:

TABLE 2

(II)

R₁—S(O)$_n$—C—[cyclohexane-1,3-dione with (A) linker]

| Comp. | R₁ | n | A | Physical data |
|---|---|---|---|---|
| 2.01 | CH₃ | 0 | (CH₂)₃ | m.p. 141–143° C. |
| 2.02 | C₂H₅ | 0 | (CH₂)₃ | m.p. 92–100° C. |
| 2.03 | CH₃ | 0 | (CH₂)₂ | m.p. 140–145° C. |
| 2.04 | C₂H₅ | 0 | (CH₂)₂ | m.p. 118–121° C. |
| 2.05 | C₃H₇-n | 0 | (CH₂)₂ | m.p. 107–109° C. |
| 2.06 | CH₃ | 0 | (CH₂)₄ | m.p. 138–140° C. |
| 2.07 | C₂H₅ | 0 | (CH₂)₄ | |
| 2.08 | C₂H₅ | 1 | (CH₃)₄ | |
| 2.09 | C₂H₅ | 2 | (CH₂)₄ | |
| 2.10 | CH₃ | 0 | (CH₂)₅ | m.p. 138–140° C. |
| 2.11 | C₂H₅ | 0 | (CH₂)₅ | m.p. 99–101° C. |
| 2.12 | C₃H₇-n | 0 | (CH₂)₅ | |
| 2.13 | benzyl | 0 | (CH₂)₅ | |
| 2.14 | CH(CH₃)₂ | 0 | (CH₂)₂ | m.p. 98–104° C. |
| 2.15 | benzyl | 0 | (CH₂)₂ | m.p. 163–165° C. |
| 2.16 | CH₃ | 1 | (CH₂)₂ | |
| 2.17 | CH₃ | 2 | (CH₂)₂ | |
| 2.18 | C₂H₅ | 1 | (CH₂)₂ | |
| 2.19 | C₂H₅ | 2 | (CH₂)₂ | |
| 2.20 | CH₃ | 1 | (CH₂)₃ | |
| 2.21 | CH₃ | 2 | (CH₂)₃ | |

EXAMPLE 3

Preparation of 5-(1-methylthiocyclobutan-1-yl)-3-n-butyryloxycyclohex-2-en-1-one (intermediate)

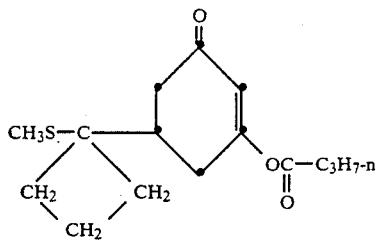

A mixture of 13.8 g of cyclohexane-1,3-dione, 8.7 g of butyryl chloride and 11.3 g of potassium carbonate in 250 ml of tetrahydrofuran is stirred for 4 hours at room temperature. The reaction mixture is then concentrated by evaporation and taken up in ether, and the resultant ethereal solution is washed twice with water and once with brine and dried. The ether is evaporated off, and the residual oil is chromatographed through a flash column packed with silica gel [eluant: a 1:2 mixture of ether and hexane]. The eluate is concentrated by evaporation, affording 10.2 g of a colourless oil; $n_{26}^D = 1.5275$.

The intermediate cyclohexanone esters of formula IV listed in Table 3 are prepared by procedures analogous to that of this Example.

TABLE 3

(IV)

R₁—S(O)$_n$—C—[cyclohexenone with O—C(=O)—R₂]

| Comp. | R₁ | n | A | R₂ | Physical data |
|---|---|---|---|---|---|
| 3.01 | CH₃ | 0 | (CH₂)₃ | C₃H₇-n | $n_D^{26}$ 1.5275 |
| 3.02 | CH₃ | 0 | (CH₂)₃ | cyclopropyl | $n_D^{35}$ 1.5478 |
| 3.03 | C₂H₅ | 0 | (CH₂)₃ | C₃H₇-n | $n_D^{35}$ 1.5218 |
| 3.04 | C₂H₅ | 0 | (CH₂)₃ | cyclopropyl | |
| 3.05 | C₂H₅ | 0 | (CH₂)₃ | C₂H₅ | $n_D^{30}$ 1.5253 |
| 3.06 | CH₃ | 0 | (CH₂)₂ | C₃H₇-n | $n_D^{26}$ 1.5210 |
| 3.07 | CH₃ | 0 | (CH₂)₂ | cyclopropyl | $n_D^{26}$ 1.5413 |
| 3.08 | C₂H₅ | 0 | (CH₂)₂ | C₃H₇-n | b.p. 142° C./0.013 mbar |
| 3.09 | C₂H₅ | 0 | (CH₂)₂ | cyclopropyl | $n_D^{25}$ 1.5358 |
| 3.10 | C₂H₅ | 0 | (CH₂)₂ | C₂H₅ | b.p. 137°/0.013 mbar |
| 3.11 | C₂H₅ | 0 | (CH₂)₂ | CH(CH₃)₂ | |
| 3.12 | CH₃ | 0 | (CH₂)₄ | C₃H₇-n | $n_D^{26}$ 1.5297 |
| 3.13 | C₂H₅ | 0 | (CH₂)₄ | C₃H₇-n | |
| 3.14 | CH₃ | 0 | (CH₂)₄ | cyclopropyl | $n_D^{26}$ 1.5437 |
| 3.15 | CH₃ | 0 | (CH₂)₂ | C₂H₅ | $n_D^{26}$ 1.5310 |
| 3.16 | C₂H₅ | 0 | (CH₂)₄ | C₂H₅ | |
| 3.17 | CH₃ | 0 | (CH₂)₅ | C₃H₇-n | $n_D^{30}$ 1.5306 |
| 3.18 | CH₃ | 0 | (CH₂)₅ | cyclopropyl | m.p. 90–91° C. |
| 3.19 | C₂H₅ | 0 | (CH₂)₅ | C₃H₇-n | $n_D^{30}$ 1.5263 |
| 3.20 | C₂H₅ | 0 | (CH₂)₅ | cyclopropyl | |
| 3.21 | CH₃ | 0 | (CH₂)₃ | benzyl | |
| 3.22 | CH₃ | 0 | (CH₂)₃ | C₂H₅ | $n_D^{26}$ 1.5356 |
| 3.23 | C₂H₅ | 0 | (CH₂)₅ | C₂H₅ | $n_D^{30}$ 1.5333 |
| 3.24 | C₂H₅ | 0 | (CH₂)₄ | CH₃ | |
| 3.25 | CH₃ | 0 | (CH₂)₅ | C₂H₅ | m.p. 76–77° C. |
| 3.26 | CH(CH₃)₂ | 0 | (CH₂)₂ | C₂H₅ | $n_D^{30}$ 1.5167 |
| 3.27 | CH(CH₃)₂ | 0 | (CH₂)₂ | C₃H₇-n | $n_D^{30}$ 1.5125 |
| 3.28 | CH(CH₃)₂ | 0 | (CH₂)₂ | cyclopropyl | $n_D^{30}$ 1.5298 |
| 3.29 | C₃H₇-n | 0 | (CH₂)₂ | C₂H₅ | b.p. 140–142° C./0.013 mbar |
| 3.30 | C₃H₇-n | 0 | (CH₂)₂ | C₃H₇-n | b.p. 153–155° C./0.013 mbar |
| 3.31 | C₃H₇-n | 0 | (CH₂)₂ | cyclopropyl | $n_D^{30}$ 1.5290 |
| 3.32 | C₃H₇-n | 0 | (CH₂)₂ | CH(CH₃)₂ | $n_D^{30}$ 1.5096 |
| 3.33 | CH₃ | 0 | (CH₂)₂ | CH₃ | $n_D^{30}$ 1.5303 |
| 3.34 | CH₃ | 0 | (CH₂)₂ | C₄H₉-n | |
| 3.35 | benzyl | 0 | (CH₂)₅ | C₂H₅ | m.p. 69–71° C. |
| 3.36 | benzyl | 0 | (CH₂)₅ | C₃H₇-n | $n_D^{30}$ 1.5562 |
| 3.37 | CH₃ | 1 | (CH₂)₂ | C₂H₅ | |
| 3.38 | CH₃ | 2 | (CH₂)₂ | C₃H₇-n | |
| 3.39 | CH₃ | 2 | (CH₂)₂ | C₂H₅ | |
| 3.40 | CH₃ | 1 | (CH₂)₂ | C₃H₇-n | |
| 3.41 | CH₃ | 1 | (CH₂)₃ | C₂H₅ | |
| 3.42 | CH₃ | 2 | (CH₂)₃ | C₃H₇-n | |
| 3.43 | benzyl | 0 | (CH₂)₂ | cyclopropyl | m.p. 62–64° C. |

EXAMPLE 4

Preparation of 5-(1-methylthiocyclobutan-1-yl)-2-n-butyrylcyclohexane-1,3-dione

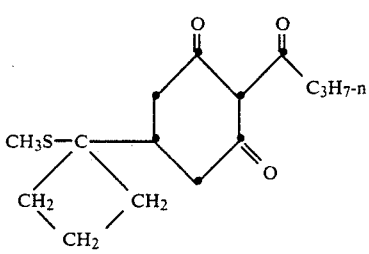

A solution of 10.0 g of 5-(1-methylthiocyclobutan-1-yl)-3-n-butyryloxycyclohex-2-en-1-one (Example 3)

and 0.5 g of 4-(N,N-dimethylamino)pyridine is stirred for 3 days at a temperature of 100°–110° C. The reaction mixture is then concentrated by evaporation. The residual oil is chromatographed through a column of 300 g of silica gel covered with a 1 cm thick layer of aluminium oxide (acidic) [eluant: a 1:5 mixture of ther and hexane]. The eluate is evaporated off, affording 8.1 g of title product in the form of a yellow oil; $n_D^{35}=1.5498$.

EXAMPLE 5

Preparation of 5-(1-methylthiocyclobutan-1-yl)-2-(2,4-dichlorobenzoylcyclohexane-1,3-dione

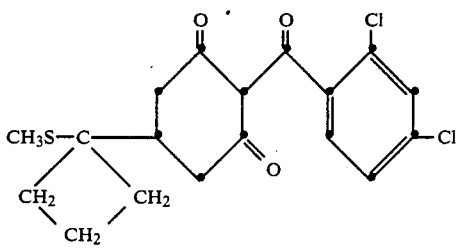

With cooling in an ice-bath and with stirring, 1.94 g of triethylamine are added dropwise to a mixture of 3.71 g of 5-(1-methylthiocyclobutan-1-yl)cyclohexane-1,3-dione (Example 2), 3.85 g of 2,4-dichlorobenzoyl cyanide and 2.62 g of zinc chloride in 100 ml of methylene chloride. The reaction mixture is then allowed to warm to room temperature, and stirring is continued for 20 hours. The reaction mixture is then poured into a 1:1 mixture of ice and concentrated hydrochloric acid. After the addition of methylene chloride, the organic phase is separated, washed twice with water, dried and concentrated by evaporation. The residue is chromatographed through a column of 150 g of silica gel covered with a 1 cm thick layer of aluminium oxide (Alox I acidic) [eluant: a 1:1 mixture of ethyl acetate and hexane]. The eluate is concentrated by evaporation, and the residue is taken up in ether. Insoluble residue is filtered off. After the ether has been evaporated off, a viscous oil which congeals on standing is obtained. The oil is triturated in hexane, affording 3.4 g of crystalline material; m.p.: 82°–83° C.

The 2-acyl-1,3-cyclohexanediones of formula Ia listed in Table 4 are prepared by procedures analogous to those of Examples 4 and 5.

TABLE 4

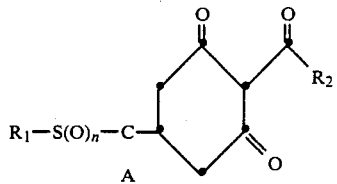

| Comp. | $R_1$ | n | A | $R_2$ | Physical data |
|---|---|---|---|---|---|
| 4.01 | $CH_3$ | 0 | $(CH_2)_3$ | $C_3H_7$-n | $n_D^{25}$ 1.5498 |
| 4.02 | $CH_3$ | 0 | $(CH_2)_3$ | cyclopropyl | $n_D^{35}$ 1.5753 |
| 4.03 | $CH_3$ | 0 | $(CH_2)_3$ | 2,4-dichlorophenyl | m.p. 82–83° C. |
| 4.04 | $CH_3$ | 0 | $(CH_2)_3$ | 2,3-dichlorophenyl | m.p. 88–91° C. |
| 4.05 | $C_2H_5$ | 0 | $(CH_2)_3$ | $C_3H_7$-n | $n_D^{30}$ 1.5432 |
| 4.06 | $C_2H_5$ | 0 | $(CH_2)_3$ | cyclopropyl | |
| 4.07 | $C_2H_5$ | 0 | $(CH_2)_3$ | 2,4-dichlorophenyl | |
| 4.08 | $C_2H_5$ | 0 | $(CH_2)_3$ | 4-chlorophenyl | |
| 4.09 | $CH_3$ | 0 | $(CH_2)_4$ | $C_3H_7$-n | $n_D^{26}$ 1.5536 |
| 4.10 | $C_2H_5$ | 0 | $(CH_2)_4$ | $C_3H_7$-n | |
| 4.11 | $C_2H_5$ | 0 | $(CH_2)_4$ | cyclopropyl | |
| 4.12 | $CH_3$ | 0 | $(CH_2)_4$ | cyclopropyl | m.p. 80–82° C. |
| 4.13 | $C_2H_5$ | 0 | $(CH_2)_4$ | 2,4-dichlorophenyl | |
| 4.14 | $CH_3$ | 0 | $(CH_2)_4$ | 2,4-dichlorophenyl | m.p. 89–91° C. |
| 4.15 | $C_2H_5$ | 0 | $(CH_2)_4$ | $C_2H_5$ | |
| 4.16 | $C_2H_5$ | 0 | $(CH_2)_4$ | $CH(CH_3)_2$ | |
| 4.17 | $C_2H_5$ | 2 | $(CH_2)_4$ | $C_3H_7$-n | |
| 4.18 | $CH_3$ | 0 | $(CH_2)_5$ | $C_3H_7$-n | $n_D^{30}$ 1.5541 |
| 4.19 | $C_2H_5$ | 0 | $(CH_2)_5$ | $C_3H_7$-n | $n_D^{30}$ 1.5483 |
| 4.20 | $C_2H_5$ | 0 | $(CH_2)_5$ | cyclopropyl | |
| 4.21 | $CH_3$ | 0 | $(CH_2)_5$ | cyclopropyl | $n_D^{30}$ 1.5711 |
| 4.22 | $C_2H_5$ | 0 | $(CH_2)_5$ | 2,4-dichlorophenyl | |
| 4.23 | $C_2H_5$ | 0 | $(CH_2)_5$ | 2-chlorophenyl | |
| 4.24 | $C_2H_5$ | 0 | $(CH_2)_5$ | $C_2H_5$ | m.p. 100–101° C. |
| 4.25 | $CH_3$ | 0 | $(CH_2)_3$ | $C_2H_5$ | $n_D^{26}$ 1.5566 |
| 4.26 | $CH_3$ | 0 | $(CH_2)_4$ | 4-chlorophenyl | m.p. 108–110° C. |
| 4.27 | $CH_3$ | 0 | $(CH_2)_2$ | cyclopropyl | m.p. 71–73° C. |
| 4.28 | $CH_3$ | 0 | $(CH_2)_2$ | $C_3H_7$-n | m.p. 61–62° C. |
| 4.29 | $CH_3$ | 0 | $(CH_2)_2$ | $C_2H_5$ | m.p. 74–76° C. |
| 4.30 | $C_2H_5$ | 0 | $(CH_2)_2$ | cyclopropyl | $n_D^{30}$ 1.5653 |
| 4.31 | $C_2H_5$ | 0 | $(CH_2)_2$ | $C_3H_7$-n | m.p. 60–61° C. |
| 4.32 | $C_2H_5$ | 0 | $(CH_2)_2$ | $C_2H_5$ | m.p. 50–51° C. |
| 4.33 | $C_2H_5$ | 0 | $(CH_2)_2$ | 2,4-dichlorophenyl | m.p. 80–82° C. |
| 4.34 | $CH_3$ | 0 | $(CH_2)_5$ | $C_2H_5$ | m.p. 69–71° C. |
| 4.35 | $CH_3$ | 0 | $(CH_2)_5$ | 2,4-dichlorophenyl | m.p. 103–106° C. |
| 4.36 | $C_2H_5$ | 0 | $(CH_2)_3$ | $C_2H_5$ | $n_D^{30}$ 1.5487 |
| 4.37 | $CH(CH_3)_2$ | 0 | $(CH_2)_2$ | $C_2H_5$ | $n_D^{30}$ 1.5398 |
| 4.38 | $CH(CH_3)_2$ | 0 | $(CH_2)_2$ | $C_3H_7$-n | $n_D^{30}$ 1.5338 |
| 4.39 | $CH(CH_3)_2$ | 0 | $(CH_2)_2$ | cyclopropyl | $n_D^{30}$ 1.5590 |
| 4.40 | $C_3H_7$-n | 0 | $(CH_2)_2$ | cyclopropyl | $n_D^{30}$ 1.5574 |
| 4.41 | $C_3H_7$-n | 0 | $(CH_2)_2$ | $CH(CH_3)_2$ | $n_D^{30}$ 1.5339 |
| 4.42 | $C_3H_7$-n | 0 | $(CH_2)_2$ | $C_3H_7$-n | b.p. 153–155°/0.013 mbar |
| 4.43 | $C_3H_7$-n | 0 | $(CH_2)_2$ | $C_2H_5$ | b.p. 150–152°/0.013 mbar |
| 4.44 | benzyl | 0 | $(CH_2)_2$ | $C_2H_5$ | $n_D^{30}$ 1.5834 |
| 4.45 | benzyl | 0 | $(CH_2)_2$ | cyclopropyl | m.p. 112–113° C. |
| 4.46 | benzyl | 0 | $(CH_2)_2$ | $C_3H_7$-n | $n_D^{30}$ 1.5752 |
| 4.47 | $CH_3$ | 0 | $(CH_2)_2$ | $C_4H_9$-n | |
| 4.48 | $CH_3$ | 0 | $(CH_2)_2$ | $CH_3$ | m.p. 80–82° C. |
| 4.49 | $CH_3$ | 1 | $(CH_2)_2$ | $C_2H_5$ | |
| 4.50 | $CH_3$ | 1 | $(CH_2)_2$ | $C_3H_7$-n | |
| 4.51 | $CH_3$ | 2 | $(CH_2)_2$ | $C_2H_5$ | |
| 4.52 | $CH_3$ | 2 | $(CH_2)_2$ | $C_3H_7$-n | |
| 4.53 | $CH_3$ | 1 | $(CH_2)_3$ | $C_2H_5$ | |
| 4.54 | $CH_3$ | 2 | $(CH_2)_3$ | $C_2H_5$ | |
| 4.55 | $CH_3$ | 1 | $(CH_2)_3$ | $C_3H_7$-n | |
| 4.56 | $CH_3$ | 2 | $(CH_2)_3$ | $C_3H_7$-n | |

EXAMPLE 6

Preparation of
5-(1-methylthiocyclobutan-1-yl)-2-(3-oxa-4-azaoct-4-en-5-yl)cyclohexane-1,3-dione
[5-(1-methylthiocyclobutan-1-yl)-2-(1-ethoximinobutyryl)cyclohexane-1,3-dione]

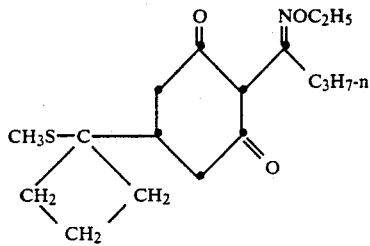

A mixture of 3.0 g of 5-(1-methylthiocyclobutan-1-yl)-2-n-butyrylcyclohexane-1,3-dione (Example 4), 1.15 g of O-ethylhydroxylamine.hydrochloride and 1.5 g of potassium carbonate in 30 ml of chloroform and 3 ml of methanol is stirred for 3 days at room temperature. The reaction mixture is then evaporated to dryness, the residue is taken up in ether, and the ethereal layer is washed first with water and then with 1N hydrochloric acid. The ethereal layer is extracted cold with 2N potassium hydroxide solution, and the aqueous layer is rewashed with ether. The basic-aqueous extract is made cold and then neutralised with ice-cold semi-concentrated hydrochloric acid to pH 5.5. Subsequently, the batch is again extracted with ether, the ethereal layer is dried over sodium sulfate and filtered, the filtrate is concentrated by evaporation, and the residue is taken up in pentane. The pentane solution is treated with active carbon and filtered, and the filtrate is concentrated by evaporation, thus affording 2.5 g of title product in the form of a colourless oil; $n_D^{30} = 1.5428$.

The oxime ethers of 2-acyl-1,3-cyclohexandiones of formula Ib listed in Table 5 are prepared by procedures analogous to that of Example 6.

TABLE 5

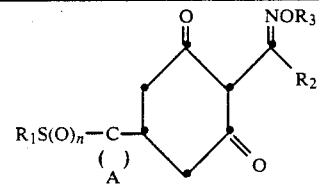

| Comp. | $R_1$ | n | A | $R_2$ | $R_3$ | Physical data |
|---|---|---|---|---|---|---|
| 5.01 | $CH_3$ | 0 | $(CH_2)_3$ | $C_3H_7$-n | $C_2H_5$ | $n_D^{30}$ 1.5428 |
| 5.02 | $CH_3$ | 0 | $(CH_2)_5$ | $C_3H_7$-n | $C_2H_5$ | $n_D^{30}$ 1.5429 |
| 5.03 | $CH_3$ | 0 | $(CH_2)_3$ | $C_3H_7$-n | $CH_2CH=CH_2$ | $n_D^{30}$ 1.5468 |
| 5.04 | $CH_3$ | 0 | $(CH_2)_3$ | $C_3H_7$-n | $CH_2CH=CHCl$ | $n_D^{31}$ 1.5541 |
| 5.05 | $C_2H_5$ | 0 | $(CH_2)_3$ | $C_3H_7$-n | $C_2H_5$ | $n_D^{30}$ 1.5356 |
| 5.06 | $C_2H_5$ | 0 | $(CH_2)_3$ | $C_2H_5$ | $C_2H_5$ | $n_D^{30}$ 1.5410 |
| 5.07 | $C_2H_5$ | 0 | $(CH_2)_3$ | $C_3H_7$-n | $C_4H_9$-n | |
| 5.08 | $C_2H_5$ | 2 | $(CH_2)_3$ | $C_3H_7$-n | $C_2H_5$ | |
| 5.09 | $CH_3$ | 2 | $(CH_2)_3$ | $C_3H_7$-n | $C_2H_5$ | |
| 5.10 | $C_2H_5$ | 0 | $(CH_2)_2$ | $C_3H_7$-n | $CH_2CH=CH_2$ | $n_D^{30}$ 1.5360 |
| 5.11 | $C_3H_7$-n | 0 | $(CH_2)_2$ | $C_2H_5$ | $C_2H_5$ | $n_D^{30}$ 1.5312 |
| 5.12 | $C_2H_5$ | 0 | $(CH_2)_2$ | $C_3H_7$-n | $CH_2CH=CHCl$ | $n_D^{30}$ 1.5460 |
| 5.13 | $CH_3$ | 0 | $(CH_2)_4$ | $C_3H_7$-n | $C_2H_5$ | $n_D^{30}$ 1.5426 |
| 5.14 | $C_2H_5$ | 0 | $(CH_2)_4$ | $C_3H_7$-n | $C_2H_5$ | |
| 5.15 | $C_2H_5$ | 0 | $(CH_2)_4$ | $C_2H_5$ | $C_2H_5$ | |
| 5.16 | $C_2H_5$ | 0 | $(CH_2)_4$ | $C_3H_7$-n | $CH_3$ | |
| 5.17 | $C_2H_5$ | 2 | $(CH_2)_4$ | $C_2H_5$ | $C_4H_9$-n | |
| 5.18 | $C_2H_5$ | 1 | $(CH_2)_4$ | $C_3H_7$-n | $C_2H_5$ | |
| 5.19 | $C_2H_5$ | 0 | $(CH_2)_5$ | $C_3H_7$-n | $C_2H_5$ | $n_D^{30}$ 1.5398 |
| 5.20 | $C_2H_5$ | 0 | $(CH_2)_5$ | $C_2H_5$ | $C_2H_5$ | $n_D^{30}$ 1.5450 |
| 5.21 | $C_2H_5$ | 0 | $(CH_2)_5$ | $C_3H_7$-n | $CH_2CH=CH_2$ | $n_D^{30}$ 1.5449 |
| 5.22 | $CH_3$ | 0 | $(CH_2)_5$ | $C_3H_7$-n | $CH_2CH=CHCl$ | $n_D^{30}$ 1.5571 |
| 5.23 | $CH_3$ | 0 | $(CH_2)_4$ | $C_3H_7$-n | $CH_2CH=CHCl$ | $n_D^{30}$ 1.5569 |
| 5.24 | $CH_3$ | 0 | $(CH_2)_4$ | $C_3H_7$-n | $CH_2CH=CH_2$ | $n_D^{30}$ 1.5480 |
| 5.25 | $CH_3$ | 0 | $(CH_2)_3$ | $C_3H_7$-n | $C_4H_9$-n | $n_D^{30}$ 1.5324 |
| 5.26 | $CH_3$ | 0 | $(CH_2)_3$ | $C_2H_5$ | $C_4H_9$-n | $n_D^{30}$ 1.5383 |
| 5.27 | $CH_3$ | 0 | $(CH_2)_2$ | $C_3H_7$-n | $C_2H_5$ | $n_D^{30}$ 1.5362 |
| 5.28 | $CH_3$ | 0 | $(CH_2)_2$ | $C_3H_7$-n | $CH_2CH=CH_2$ | $n_D^{30}$ 1.5420 |
| 5.29 | $CH_3$ | 0 | $(CH_2)_2$ | $C_3H_7$-n | $CH_2CH=CHCl$ | $n_D^{30}$ 1.5514 |
| 5.30 | $C_2H_5$ | 0 | $(CH_2)_2$ | $C_3H_7$-n | $C_2H_5$ | $n_D^{30}$ 1.5302 |
| 5.31 | $CH_3$ | 0 | $(CH_2)_2$ | $C_2H_5$ | $C_2H_5$ | m.p. 65-69° C. |
| 5.32 | $C_2H_5$ | 0 | $(CH_2)_2$ | $C_2H_5$ | $C_2H_5$ | $n_D^{30}$ 1.5359 |
| 5.33 | $C_2H_5$ | 0 | $(CH_2)_2$ | $C_2H_5$ | $C_4H_9$-n | $n_D^{30}$ 1.5288 |
| 5.34 | $C_2H_5$ | 0 | $(CH_2)_3$ | $C_2H_5$ | $CH_2CH=CHCl$ | $n_D^{30}$ 1.5558 |
| 5.35 | $C_2H_5$ | 0 | $(CH_2)_3$ | $C_3H_7$-n | $CH_2CH=CHCl$ | $n_D^{30}$ 1.5496 |
| 5.36 | $CH_3$ | 0 | $(CH_2)_3$ | $C_2H_5$ | $CH_3$ | $n_D^{30}$ 1.5539 |
| 5.37 | $CH_3$ | 0 | $(CH_2)_3$ | $C_2H_5$ | $C_2H_5$ | $n_D^{30}$ 1.5469 |
| 5.38 | $CH_3$ | 0 | $(CH_2)_3$ | $C_2H_5$ | $CH_2CH=CHCl$ | $n_D^{30}$ 1.5613 |
| 5.39 | $CH_3$ | 0 | $(CH_2)_2$ | $C_2H_5$ | $CH_2CH=CHCl$ | $n_D^{30}$ 1.5568 |
| 5.40 | $C_2H_5$ | 0 | $(CH_2)_2$ | $C_3H_7$-n | $C_4H_9$-n | $n_D^{30}$ 1.5242 |
| 5.41 | $C_2H_5$ | 0 | $(CH_3)_2$ | $C_2H_5$ | $CH_2CH=CH_2$ | $n_D^{30}$ 1.5407 |
| 5.42 | $C_2H_5$ | 0 | $(CH_3)_2$ | $C_2H_5$ | $CH_2CH=CHCl$ | $n_D^{30}$ 1.5514 |
| 5.43 | $C_2H_5$ | 0 | $(CH_2)_5$ | $C_3H_7$-n | $C_4H_9$-n | $n_D^{30}$ 1.5379 |
| 5.44 | $CH_3$ | 0 | $(CH_2)_5$ | $C_2H_5$ | $C_2H_5$ | $n_D^{30}$ 1.5496 |
| 5.45 | $CH_3$ | 0 | $(CH_2)_5$ | $C_2H_5$ | $CH_2CH=CH_2$ | $n_D^{30}$ 1.5547 |

TABLE 5-continued

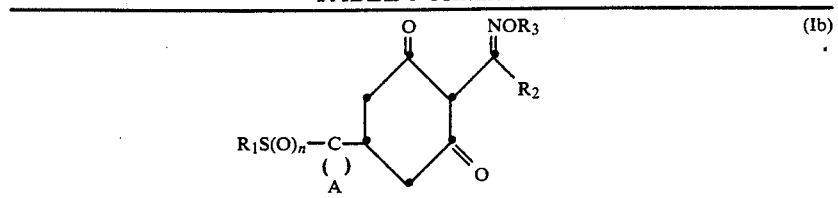

(Ib)

| Comp. | R₁ | n | A | R₂ | R₃ | Physical data |
|---|---|---|---|---|---|---|
| 5.46 | CH₃ | 0 | (CH₂)₅ | C₂H₅ | CH₂CH=CHCl | $n_D^{30}$ 1.5631 |
| 5.47 | CH₃ | 0 | (CH₂)₅ | C₂H₅ | C₄H₉-n | $n_D^{30}$ 1.5415 |
| 5.48 | CH₃ | 0 | (CH₂)₅ | C₂H₅ | CH₃ | $n_D^{30}$ 1.5565 |
| 5.49 | C₂H₅ | 0 | (CH₂)₅ | C₃H₇-n | CH₂CH=CHCl | $n_D^{30}$ 1.5526 |
| 5.50 | CH₃ | 0 | (CH₂)₂ | C₂H₅ | CH₂CH=CHCl | (trans) $n_D^{30}$ 1.5578 |
| 5.51 | CH₃ | 0 | (CH₃)₂ | C₂H₅ | CH₂CH=CHCl | (cis) $n_D^{30}$ 1.5570 |
| 5.52 | C₂H₅ | 0 | (CH₂)₂ | C₂H₅ | CH₂CH=CHCl | (trans) $n_D^{30}$ 1.5519 |
| 5.53 | C₂H₅ | 0 | (CH₂)₂ | C₃H₇-n | CH₂CH=CHCl | (trans) $n_D^{30}$ 1.5464 |
| 5.54 | C₂H₅ | 0 | (CH₂)₂ | C₂H₅ | CH₂CH=CHCl | (cis) $n_D^{30}$ 1.5511 |
| 5.55 | C₂H₅ | 0 | (CH₂)₂ | C₃H₇-n | CH₂CH=CHCl | (cis) $n_D^{30}$ 1.5460 |
| 5.56 | CH₃ | 0 | (CH₂)₂ | C₂H₅ | CH₃ | $n_D^{30}$ 1.5491 |
| 5.57 | CH₃ | 0 | (CH₂)₂ | C₂H₅ | CH₂CH=CH₂ | m.p. 46–49° C. |
| 5.58 | CH₃ | 0 | (CH₂)₂ | C₃H₇-n | CH₂CH=CHCl | (trans) $n_D^{30}$ 1.5516 |
| 5.59 | CH₃ | 0 | (CH₂)₂ | C₃H₇-n | CH₂CH=CHCl | (cis) $n_D^{30}$ 1.5510 |
| 5.60 | CH(CH₃)₂ | 0 | (CH₂)₂ | C₂H₅ | C₂H₅ | $n_D^{30}$ 1.5315 |
| 5.61 | CH(CH₃)₂ | 0 | (CH₂)₂ | C₂H₅ | CH₂CH=CH₂ | $n_D^{30}$ 1.5372 |
| 5.62 | CH(CH₃)₂ | 0 | (CH₂)₂ | C₂H₅ | CH₂CH=CHCl | (trans) $n_D^{30}$ 1.5469 |
| 5.63 | CH(CH₃)₂ | 0 | (CH₂)₂ | C₃H₇-n | C₂H₅ | $n_D^{30}$ 1.5258 |
| 5.64 | CH(CH₃)₂ | 0 | (CH₂)₂ | C₃H₇-n | CH₂CH=CH₂ | $n_D^{30}$ 1.5322 |
| 5.65 | CH(CH₃)₂ | 0 | (CH₂)₂ | C₃H₇-n | CH₂CH=CHCl | (trans) $n_D^{30}$ 1.5431 |
| 5.66 | CH(CH₃)₂ | 0 | (CH₂)₂ | C₃H₇-n | CH₃ | $n_D^{30}$ 1.5313 |
| 5.67 | CH₃ | 0 | (CH₂)₂ | C₂H₅ | CH₂CCl=CH₂ | $n_D^{30}$ 1.5538 |
| 5.68 | C₃H₇-n | 0 | (CH₂)₂ | C₂H₅ | CH₂CH=CHCl | (trans) $n_D^{30}$ 1.5472 |
| 5.69 | C₃H₇-n | 0 | (CH₂)₂ | C₂H₅ | CH₂CCl=CH₂ | $n_D^{30}$ 1.5440 |
| 5.70 | C₃H₇-n | 0 | (CH₂)₂ | C₂H₅ | CH₂CH=CH₂ | $n_D^{30}$ 1.5370 |
| 5.71 | C₃H₇-n | 0 | (CH₂)₂ | C₃H₇-n | C₂H₅ | $n_D^{30}$ 1.5268 |
| 5.72 | C₃H₇-n | 0 | (CH₂)₂ | C₃H₇-n | CH₂CH=CHCl | (trans) $n_D^{30}$ 1.5420 |
| 5.73 | C₃H₇-n | 0 | (CH₂)₂ | C₃H₇-n | CH₂CCl=CH₂ | $n_D^{30}$ 1.5390 |
| 5.74 | C₃H₇-n | 0 | (CH₂)₂ | C₃H₇-n | C₄H₉-n | $n_D^{30}$ 1.5208 |
| 5.75 | CH₃ | 0 | (CH₂)₂ | C₂H₅ | CH₂CBr=CH₂ | |
| 5.76 | benzyl | 0 | (CH₂)₂ | C₂H₅ | C₂H₅ | m.p. 115–117° C. |
| 5.77 | benzyl | 0 | (CH₂)₂ | C₂H₅ | CH₂CH=CHCl | (trans) $n_D^{30}$ 1.5792 |
| 5.78 | benzyl | 0 | (CH₂)₂ | C₃H₇-n | C₂H₅ | $n_D^{30}$ 1.5478 |
| 5.79 | benzyl | 0 | (CH₂)₂ | C₃H₇-n | CH₂CH=CHCl | (trans) $n_D^{30}$ 1.5706 |
| 5.80 | CH₃ | 0 | (CH₂)₂ | C₂H₅ | C₃H₇-n | |
| 5.81 | CH₃ | 0 | (CH₂)₂ | C₂H₅ | C₄H₉-n | $n_D^{30}$ 1.5323 |
| 5.82 | CH₃ | 0 | (CH₂)₂ | C₂H₅ | CH₂C≡CH | $n_D^{30}$ 1.5533 |
| 5.83 | CH₃ | 1 | (CH₂)₂ | C₂H₅ | CH₂CH=CHCl | (trans) $n_D^{30}$ 1.5640 |
| 5.84 | CH₃ | 2 | (CH₂)₂ | C₂H₅ | CH₂CH=CHCl | (trans) $n_D^{40}$ 1.5500 |
| 5.85 | CH₃ | 0 | (CH₂)₂ | C₃H₇-n | CH₂CCl=CH₂ | $n_D^{30}$ 1.5487 |
| 5.86 | CH₃ | 0 | (CH₂)₂ | C₃H₇-n | C₃H₇-n | |
| 5.87 | CH₃ | 0 | (CH₂)₂ | C₃H₇-n | CH₂C≡CH | $n_D^{30}$ 1.5476 |
| 5.88 | CH₃ | 0 | (CH₂)₂ | CH₃ | CH₃ | |
| 5.89 | CH₃ | 0 | (CH₂)₂ | C₂H₅ | CH₂CH=CHBr | (trans) |
| 5.90 | CH₃ | 0 | (CH₂)₂ | C₂H₅ | CH₂CH=CHBr | $n_D^{30}$ 1.5679 |
| 5.91 | CH₃ | 0 | (CH₂)₂ | CH₃ | C₂H₅ | $n_D^{30}$ 1.5469 |
| 5.92 | CH₃ | 0 | (CH₂)₂ | C₃H₇-n | CH₂CH=CHBr | (trans) |
| 5.93 | CH₃ | 0 | (CH₂)₂ | C₃H₇-n | CH₂CH=CHBr | $n_D^{30}$ 1.5619 |
| 5.94 | CH₃ | 0 | (CH₂)₂ | CH₃ | CH₂CH=CHCl | (trans) $n_D^{30}$ 1.5637 |
| 5.95 | CH₃ | 0 | (CH₂)₃ | C₂H₅ | CH₂CH=CHCl | (trans) $n_D^{25}$ 1.5618 |
| 5.96 | CH₃ | 0 | (CH₂)₃ | C₃H₇-n | CH₂CH=CHCl | (trans) $n_D^{25}$ 1.5568 |
| 5.97 | CH₃ | 1 | (CH₂)₂ | C₃H₇-n | C₂H₅ | |
| 5.98 | CH₃ | 2 | (CH₂)₂ | C₃H₇-n | C₂H₅ | |
| 5.99 | CH₃ | 0 | (CH₂)₂ | C₄H₉-n | CH₂CH=CHCl | (trans) |
| 5.100 | CH₃ | 0 | (CH₂)₂ | C₄H₉-n | C₂H₅ | |
| 5.101 | CH₃ | 0 | (CH₂)₂ | C₂H₅ | CH₂CH=CCl₂ | $n_D^{30}$ 1.5609 |
| 5.102 | C₂H₅ | 0 | (CH₂)₂ | C₂H₅ | CH₂CH=CCl₂ | |
| 5.103 | CH₃ | 0 | (CH₂)₂ | C₃H₇-n | CH₂CH=CCl₂ | |
| 5.104 | C₂H₅ | 0 | (CH₂)₂ | C₃H₇-n | CH₂CH=CCl₂ | |
| 5.105 | CH₃ | 0 | (CH₂)₂ | C₂H₅ | CH₂CCl=CClH | |
| 5.106 | C₂H₅ | 0 | (CH₂)₂ | C₂H₅ | CH₂CCl=CHCl | |
| 5.107 | CH₃ | 0 | (CH₂)₂ | C₃H₇-n | CH₂CCl=CHCl | |
| 5.108 | C₂H₅ | 0 | (CH₂)₂ | C₃H₇-n | CH₂CCl=CHCl | |
| 5.109 | CH₃ | 0 | (CH₂)₂ | C₂H₅ | CH₂CH=CHCH₃ | (trans) $n_D^{30}$ 1.5450 |
| 5.110 | C₂H₅ | 0 | (CH₂)₂ | C₂H₅ | CH₂CH=CHCH₃ | (trans) |
| 5.111 | CH₃ | 0 | (CH₂)₂ | C₃H₇-n | CH₂CH=CHCH₃ | (trans) $n_D^{30}$ 1.5401 |
| 5.112 | C₂H₅ | 0 | (CH₂)₂ | C₃H₇-n | CH₂CH=CHCH₃ | (trans) |
| 5.113 | CH₃ | 0 | (CH₃)₂ | C₂H₅ | CH₂CH=CClCH₃ | $n_D^{30}$ 1.5543 |
| 5.114 | CH₃ | 0 | (CH₃)₂ | C₂H₅ | CH₂CH=CClCH₃ | |
| 5.115 | C₂H₅ | 0 | (CH₃)₂ | C₂H₅ | CH₂CH=CClCH₃ | (trans) |
| 5.116 | C₂H₅ | 0 | (CH₃)₂ | C₂H₅ | CH₂CH=CClCH₃ | |

TABLE 5-continued (Ib)

structure: cyclohexane-1,3-dione with R1S(O)n—C attached at position 5 (ring labeled A), and at position 2 a C(=NOR3)—R2 substituent.

| Comp. | R1 | n | A | R2 | R3 | Physical data |
|---|---|---|---|---|---|---|
| 5.117 | CH3 | 0 | (CH2)2 | C3H7-n | CH2CH=CClCH3 | (trans) |
| 5.118 | CH3 | 0 | (CH2)2 | C3H7-n | CH2CH=CClCH3 | |
| 5.119 | C2H5 | 0 | (CH2)2 | C3H7-n | CH2CH=CClCH3 | (trans) |
| 5.120 | C2H5 | 0 | (CH2)2 | C3H7-n | CH2CH=CClCH3 | |
| 5.121 | CH3 | 0 | (CH2)2 | C2H5 | CH2CHClCH=CH2 | |
| 5.122 | C2H5 | 0 | (CH2)2 | C2H5 | CH2CHClCH=CH2 | |
| 5.123 | CH3 | 0 | (CH2)2 | C3H7-n | CH2CHClCH=CH2 | |
| 5.124 | C2H5 | 0 | (CH2)2 | C3H7-n | CH2CHClCH=CH2 | |
| 5.125 | CH3 | 0 | (CH2)2 | C2H5 | CH2CH=CHCH2Cl | |
| 5.126 | CH3 | 0 | (CH2)2 | C3H7-n | CH2CH=CHCH2Cl | |
| 5.127 | CH3 | 0 | (CH2)2 | C2H5 | CH2CH2CH2Cl | |
| 5.128 | CH3 | 0 | (CH2)2 | C3H7-n | CH2CH2CH2Cl | |
| 5.129 | CH3 | 0 | (CH2)2 | C2H5 | CH2CH2Cl | |
| 5.130 | CH3 | 0 | (CH2)2 | C2H5 | CH2CH(CH3)2 | |
| 5.131 | CH3 | 0 | (CH2)2 | C3H7-n | CH2CH(CH3)2 | |
| 5.132 | CH3 | 0 | (CH2)2 | CH2OCH3 | CH2CH=CHCl | (trans) |
| 5.133 | CH3 | 0 | (CH2)2 | benzyl | CH2CH=CHCl | (trans) |
| 5.134 | CH3 | 0 | (CH2)2 | phenylether | CH2CH=CHCl | (trans) |
| 5.135 | CH3 | 0 | (CH2)2 | C2F5 | C2H5 | |
| 5.136 | CH3 | 0 | (CH2)2 | C2F5 | CH2CH=CHCl | (trans) |
| 5.137 | CH3 | 0 | (CH2)2 | C3F7-n | CH2CH=CHCl | (trans) |
| 5.138 | CH3 | 0 | (CH2)2 | C3F7-n | C2H5 | |
| 5.139 | CH3 | 0 | (CH2)2 | CF3 | C2H5 | |
| 5.140 | CH3 | 0 | (CH2)2 | C2H5 | CH2CCl=CClCH3 | (trans) |
| 5.141 | CH3 | 0 | (CH2)2 | C3H7-n | CH2CCl=CClCH3 | (trans) |
| 5.142 | CH3 | 0 | (CH2)2 | C2H5 | CH2CCl=CClCH3 | (cis) |
| 5.143 | CH3 | 0 | (CH2)2 | C3H7-n | CH2CCl=CClCH3 | (cis) |
| 5.144 | CH3 | 0 | (CH2)5 | C3H7-n | CH2—CH=CH2 | $n_D^{30}$ 1.5491 |
| 5.145 | CH3 | 0 | (CH2)2 | CH3 | CH2—CCl=CH2 | $n_D^{30}$ 1.5592 |
| 5.146 | benzyl | 0 | (CH2)2 | C2H5 | C4H9-n | m.p. 57–59° C. |
| 5.147 | benzyl | 0 | (CH2)2 | C2H5 | CH2CH=CH2 | m.p. 85–87° C. |
| 5.148 | benzyl | 0 | (CH2)2 | C3H7-n | C4H9-n | $n_D^{30}$ 1.5472 |
| 5.149 | benzyl | 0 | (CH2)2 | C3H7-n | CH2—CH=CH2 | $n_D^{30}$ 1.5490 |
| 5.150 | CH3 | 0 | (CH2)2 | C2H5 | CH2—C≡C—CH3 | |
| 5.151 | CH3 | 0 | (CH2)3 | C2H5 | CH2—CH=CHBr | |
| 5.152 | CH3 | 0 | (CH2)3 | C2H5 | CH2—C≡CH | |
| 5.153 | CH3 | 0 | (CH2)3 | C2H5 | CH2CCl=CH2 | |
| 5.154 | CH3 | 0 | (CH2)3 | C2H5 | CH2—CH=CHCH3 | (trans) |
| 5.155 | CH3 | 0 | (CH2)3 | C3H7(n) | CH2—CH=CHBr | |
| 5.156 | CH3 | 0 | (CH2)3 | C3H7(n) | CH2—C≡CH | |
| 5.157 | CH3 | 0 | (CH2)3 | C3H7(n) | CH2—CCl=CH2 | |
| 5.158 | CH3 | 0 | (CH2)3 | C3H7(n) | CH2—CH=CH—CH3 | (trans) |
| 5.159 | C2H5 | 0 | (CH2)3 | C3H7(n) | CH2—CH=CHCl | (trans) $n_D^{30}$ 1.5505 |
| 5.160 | CH3 | 0 | (CH2)3 | C2H5 | CH2—CH=CHCl | $n_D^{25}$ 1.5614 |
| 5.161 | CH3 | 0 | (CH2)3 | C3H7(n) | CH2—CH=CHCl | (cis) $n_D^{25}$ 1.5564 |
| 5.162 | C2H5 | 0 | (CH2)2 | C2H5 | CH2—CH=CHCl | (trans) $n_D^{25}$ 1.5580 |
| 5.163 | CH3 | 0 | (CH2)2 | C2H5 | CH2CH=C(CH3)2 | $n_D^{30}$ 1.5460 |
| 5.164 | CH3 | 0 | (CH2)2 | C2H5 | CH2—CF=CHCH3 | (trans) $n_D^{30}$ 1.5381 |
| 5.165 | CH3 | 0 | (CH2)2 | C2H3 | CH2—CCl=CCl2 | $n_D^{30}$ 1.5619 |

EXAMPLE 7

Sodium 2-[1-(3-trans-chloroallyloxyamino)propylidene]-3-oxo-5-(1-methylthio-1-cyclopropyl)-cyclohex-1-en-1-olate

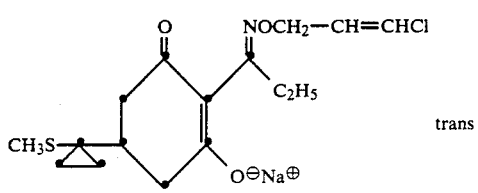

trans

A solution of 0.015 g (0.04 Mol) sodium hydroxide in 3 ml of water are added, while stirring vigorously to a solution of 5.16 g (0.015 Mol) 2-[1-(3-trans-chloroallyloxyamino)-propyliden]-5-(1-methylthio-1-cyclohexan-1,3-dion in 10 ml of tetrahydrofuran. Stirring is continued for 5 minutes and the solution is then evaporated to dryness in a rotatory evaporator at 50° C. The residue is dryed under high vacuum during 6 hours. The sodium salt is obtained in the form of a dry foam which still contains ¼ molecule of tetrahydrofuran. The salts listed in Table 6 are prepared in accordance with the method of Example 7.

TABLE 6

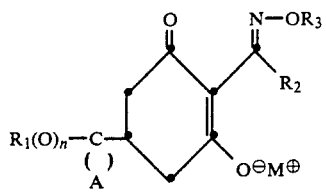

| No. | $R_1$ | n | A | $R_2$ | $R_3$ | M | phys. Daten |
|---|---|---|---|---|---|---|---|
| 6.01 | $CH_3$ | 0 | $(CH_2)_2$ | $CH_2CH=CHCl$ trans | $C_2H_5$ | $Na^\oplus$ | solid foam |
| 6.02 | $CH_3$ | 0 | $(CH_2)_2$ | $CH_2CH=CHCl$ trans | $C_2H_5$ | $K^\oplus$ | |
| 6.03 | $CH_3$ | 0 | $(CH_2)_2$ | $CH_2CH=CHCl$ trans | $C_2H_5$ | $Li^\oplus$ | solid foam |
| 6.04 | $CH_3$ | 0 | $(CH_2)_2$ | $CH_2CH=CHCl$ trans | $C_2H_5$ | $\frac{1}{2} Ca^{2\oplus}$ | |
| 6.05 | $CH_3$ | 0 | $(CH_2)_2$ | $CH_2CH=CHCl$ trans | $C_2H_5$ | $NH_4$ | |
| 6.06 | $CH_3$ | 0 | $(CH_2)_2$ | $CH_2CH=CHCl$ trans | $C_2H_5$ | $NH_3CH_3$ | |
| 6.07 | $CH_3$ | 0 | $(CH_2)_2$ | $CH_2CH=CHCl$ trans | $C_2H_5$ | $NH_2(CH_3)_2$ | |
| 6.08 | $CH_3$ | 0 | $(CH_2)_2$ | $CH_2CH=CHCl$ trans | $C_2H_5$ | $NH_2(C_2H_5)_2$ | |
| 6.09 | $CH_3$ | 0 | $(CH_2)_2$ | $CH_2CH=CHCl$ trans | $C_2H_5$ | $NH_3C_2H_5$ | |
| 6.10 | $CH_3$ | 0 | $(CH_2)_2$ | $CH_2CH=CHCl$ trans | $C_2H_5$ | $NH_2(C_3H_7iso)_2$ | |
| 6.11 | $CH_3$ | 0 | $(CH_2)_2$ | $CH_2CH=CHCl$ trans | $C_2H_5$ | $N(CH_3)_3C_2H_4OH$ | |
| 6.12 | $CH_3$ | 0 | $(CH_2)_3$ | $CH_2CH=CHCl$ trans | $C_2H_5$ | $Li^\oplus$ | |
| 6.13 | $CH_3$ | 0 | $(CH_2)_2$ | $C_2H_5$ | $C_2H_5$ | $Li^\oplus$ | |
| 6.14 | $CH_3$ | 0 | $(CH_2)_2$ | $CH_2CH=CHCl$ trans | $C_2H_5$ | $\frac{1}{2} Cu^{2\oplus}$ | |
| 6.15 | $CH_3$ | 0 | $(CH_2)_2$ | $CH_2CH=CHCl$ trans | $C_2H_5$ | $\frac{1}{2} Mg^{2\oplus}$ | |
| 6.16 | $CH_3$ | 0 | $(CH_2)_2$ | $CH_2CH=CHCl$ trans | $C_2H_5$ | $\frac{1}{2} Zn^{2\oplus}$ | |
| 6.17 | $CH_3$ | 0 | $(CH_2)_2$ | $CH_2CH=CHCl$ trans | $C_2H_5$ | $NH_3C_3H_7iso$ | |
| 6.18 | $CH_3$ | 0 | $(CH_2)_2$ | $CH_2CH=CHCl$ trans | $C_2H_5$ | $NH_3C_3H_7$-n | |
| 6.19 | $CH_3$ | 0 | $(CH_2)_2$ | $CH_2CH=CHCl$ trans | $C_3H_7$-n | $Na^\oplus$ | |
| 6.20 | $CH_3$ | 0 | $(CH_2)_2$ | $C_2H_5$ | $C_3H_7$-n | $Na^\oplus$ | |
| 6.21 | $C_2H_5$ | 0 | $(CH_2)_2$ | $C_2H_5$ | $C_2H_5$ | $Na^\oplus$ | |
| 6.22 | $C_2H_5$ | 0 | $(CH_2)_2$ | $CH_2CH=CHCl$ trans | $C_2H_5$ | $Na^\oplus$ | |
| 6.23 | $C_2H_5$ | 0 | $(CH_2)_2$ | $CH_2CH=CHCl$ trans | $C_3H_7$-n | $Na^\oplus$ | |
| 6.24 | $C_2H_5$ | 0 | $(CH_2)_2$ | $C_2H_5$ | $C_3H_7$-n | $Na^\oplus$ | |
| 6.25 | $CH_3$ | 0 | $(CH_2)_2$ | $CH_2CH=CHCl$ trans | $C_2H_5$ | $\frac{1}{2} Ba^{2\oplus}$ | |
| 6.26 | $CH_3$ | 0 | $(CH_2)_2$ | $CH_2CH=CHCl$ trans | $C_2H_5$ | $N(CH_3)_3benzyl$ | |
| 6.27 | $CH_3$ | 0 | $(CH_2)_2$ | $CH_2CH=CHCH_3$ trans | $C_2H_5$ | $Na^\oplus$ | |

EXAMPLE 8

Formulation Examples for Compounds of Formula I
(Percentages are by Weight)

| (a) Wettable powders | (a) | (b) | (c) |
|---|---|---|---|
| compound of Table 4 or 5 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants, and the mixture is thoroughly ground in a suitable mill, affording wettable powders which can be diluted with water to give suspensions of the desired concentration.

| (b) Emulsifiable concentrates | (a) | (b) |
|---|---|---|
| compound of Table 4 or 5 | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of Table 4 or 5 | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulates | (a) | (b) |
|---|---|---|
| compound of Table 4 or 5 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of Table 4 or 5 | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | (a) | (b) |
|---|---|---|
| compound of Table 4 or 5 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of Table 4 or 5 | 5% |
| isopropylamine | 1% |
| octylphenol polyethylene glycol ether (78 moles of ethylene oxide) | 3% |
| water | 91% |

EXAMPLE 9

Preemergence Herbicidal Action

In a greenhouse, plant seeds are sown in flower pots of 11 cm diameter. Immediately after sowing, the surface of the soil is treated with an aqueous emulsion of the test compounds. A concentration of 4 kg of test compound per hectare is applied. The pots are then kept in the greenhouse at 22°-25° C. and 50-70% relative humidity. 3 weeks later the test is evaluated and the action on the test plants is assessed. In this test, compounds of Tables 4 and 5 exhibit good activity, in particular against the monocotyledenous test plants.

EXAMPLE 10

Postemergence Herbicidal Action

In a greenhouse, various cultivated plants and weeds are reared from seeds, in pots, until they have reached the 4- to 6-leaf stage. The plants are then sprayed with aqueous emulsions of the test compounds (obtained from a 25% emulsifiable concentrate) at a rate of application of 4 kg/ha. The treated plants are then kept at optimum conditions of light, regular watering, temperature (22°-25° C.) and relative humidity (50-70%). The test is evaluated 15 days after treatment. The state of the plants is assessed according to the following scale
9 plant grows normally, like untreated control
7-8 slight phytotoxic symptoms
6 phytotoxic symptoms, the plant can recover
5 plant stunted
4 phytotoxic damage
2-3 severe damage
1 plant withered.

In this test compound 5.50 has been compared with 3 known compounds:

A 5-(2-ethylthioprop-1-yl)-2[1-(ethoximino)butyryl]-cyclohexane-1,3-dione, known from U.S. Pat. No. 4,249,937, Example 1

B 5-(2-ethylthioprop-1-yl)-2[1-(trans-3-chloroallyloximino)butyryl]-cyclohexane-1,3-dione, known from U.S. Pat. No. 4,440,556, compound 54

C 5-(2-ethylthioprop-1-yl)-2[1-(trans-3-chloroallyloximino)propionyl]-cyclohexane-1,3-dione, known from DE-A No. 3,627,410, Example 3.

| plant | application rate | Compound tested |||| 
|---|---|---|---|---|---|
| | | 5.50 | A | B | C |
| Avena fatua | 250 g/ha | 1 | 2 | 1 | 1 |
| | 125 g/ha | 1 | 9 | 1 | 2 |
| | 60 g/ha | 1 | 9 | 6 | 9 |
| | 30 g/ha | 1 | 9 | 8 | 9 |
| Bromus tectorum | 250 g/ha | 1 | 3 | 3 | 1 |
| | 125 g/ha | 2 | 8 | 4 | 2 |
| | 60 g/ha | 2 | 9 | 7 | 3 |
| | 30 g/ha | 5 | 9 | 9 | 9 |
| Lolium perenne | 250 g/ha | 1 | 1 | 1 | 2 |
| | 125 g/ha | 1 | 3 | 1 | 3 |
| | 60 g/ha | 1 | 4 | 4 | 7 |
| | 30 g/ha | 1 | 7 | 7 | 8 |
| Alopecurus myosuroides | 250 g/ha | 1 | 2 | 1 | 2 |
| | 125 g/ha | 1 | 3 | 2 | 2 |
| | 60 g/ha | 2 | 9 | 4 | 3 |
| | 30 g/ha | 2 | 9 | 6 | 4 |
| Digitaria sanguinalis | 250 g/ha | 1 | 3 | 1 | 1 |
| | 125 g/ha | 1 | 4 | 3 | 3 |
| | 60 g/ha | 2 | 6 | 8 | 5 |
| | 30 g/ha | 3 | 9 | 9 | 8 |
| Echinochloa crus galli | 250 g/ha | 1 | 1 | 1 | 1 |
| | 125 g/ha | 1 | 4 | 4 | 1 |
| | 60 g/ha | 1 | 6 | 6 | 4 |
| | 30 g/ha | 3 | 9 | 8 | 7 |
| Sorghum halepense | 250 g/ha | 1 | 2 | 3 | 1 |
| | 125 g/ha | 1 | 5 | 5 | 1 |
| | 60 g/ha | 2 | 7 | 7 | 4 |
| | 30 g/ha | 4 | 9 | 9 | 7 |

In this test, the compound 5.50 is herbicidally active at 30 g/ha, concentration at which the phytotoxic activity of the other compounds is low or inexistant.

EXAMPLE 11

Growth Inhibition of Tropical Leguminous Cover Crops

The test plants (Centrosema plumieri and Centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test, a marked reduction in new growth of the plants treated with compounds of Tables 4 and 5 is observed (less than 20% of the new growth of untreated control plants), without damage being caused to the test plants.

EXAMPLE 12

Growth Regulation of Soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 2000 g a.i. per hectare. Evaluation is made about 5 weeks after application of the test compound. Compared with untreated control plants, there is a marked increase in the number and weight of the siliquae on plants which have been treated with compounds of Tables 4 and 5.

EXAMPLE 13

Growth Inhibition of Cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of formula I. The concentration corresponds to up to 3000 g of active ingredient per hectare. Evaluation of the growth of the cereals is made 21 days after application. A comparison with untreated controls shows that the new growth of treated cereal plants is reduced (60-90% of the controls) and that the diameter of the stalks has in some cases increased.

EXAMPLE 14

Growth Inhibition of Grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to a rate of application of up to 3000 g a.i. per hectare. The growth of the grasses is evaluated 21 days after application. The test compounds of Tables 4 and 5 effect a reduction in new growth in the range of 10-30% in comparison with untreated controls.

What is claimed is:

1. A compound of the formula IV

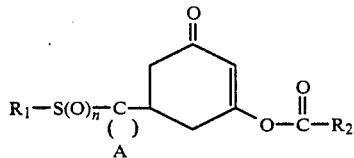

wherein

A is a 2- to 7-membered alkylene bridge, or a 3- to 7-membered alkenylene bridge which may be mono- or polyunsaturated, n is 0, 1 or 2, $R_1$ is $C_1$-$C_4$alkyl or benzyl and $R_2$ is $C_1$-$C_6$alkyl which is unsubstituted or substituted by halogen, $C_1$-$C_4$alkoxy or $C_1$-$C_4$alkylthio; or is $C_3$-$C_6$cycloalkyl; or phenyl, benzyl or phenylethyl, the phenyl ring of each of which may be substituted by halogen, $C_1$-$C_4$alkyl, $C_1$-$C_4$alkoxy, $C_1$-$C_4$alkylthio, $C_1$-$C_4$haloalkyl, $C_1$-$C_4$haloalkoxy, cyano or nitro.

2. A compound according to claim 1, wherein A is an ethylene, propylene or butylene bridge, $R_1$ is methyl or ethyl, n is zero and $R_2$ is ethyl, n-propyl, isopropyl, cyclopropyl, cyclobutyl or cyclopentyl.

3. A compound according to claim 1 selected from the group consisting of 5-(1-methylthiocyclobutan-1-yl)-3-n-butyryloxy-cyclohex-2-en-1-one, 5-(1-methylthiocyclobutan-1-yl)-3-cyclobutyryloxy-cyclohex-2-en-1-one, 5-(1-ethylthiocyclobutan-1-yl)-3-n-butyryloxy-cyclohex-2-en-1-one, 5-(1-ethylthiocyclobutan-1-yl)-3-cyclobutyryloxy-cyclohex-2-en-1-one, 5-(1-ethylthiocyclobutan-1-yl)-3-n-propionyloxy-cyclohex-2-en-1-one, 5-(1-methylthiocyclopropan-1-yl)-3-n-butyryloxy-cyclohex-2-en-1-one, 5-(1-methylthiocyclopropan-1-yl)-3-cyclopropionyloxy-cyclohex-2-en-1-one, 5-(1-ethylthiocyclopropan-1-yl)-3-n-butyryloxy-cyclohex-2-en-1-one, 5-(1-ethylthiocyclopropyn-1-yl)-3-cyclopropionyloxy-cyclohex-2-en-1-one, 5-(1-ethylthiocyclopropan-1-yl)-3-propionyloxy-cyclohex-2-en-1-one, 5-(1-ethylthiocyclopropan-1-yl)-3-isopropionyloxy-cyclohex-2-en-1-one, 5-(1-methylthiocyclopentan-1-yl)-3-n-butyryloxy-cyclohex-2-en-1-one, 5-(1-ethylthiocyclopentan-1-yl)-3-n-butyryloxy-cyclohex-2-en-1-one, 5-(1-methylthiocyclopentan-1-yl)-3-cyclopropionyloxy-cyclohex-2-en-1-one and 5-(1-methylthiocyclopropan-1-yl)-3-n-propionyloxy-cyclohex-2-en-1-one.

4. A compound according to claim 2, wherein A is the ethylene bridge, n is 0, $R_1$ is methyl or ethyl and $R_2$ is ethyl or n-propyl.

* * * * *